United States Patent
Holmes et al.

(10) Patent No.: US 11,518,762 B2
(45) Date of Patent: Dec. 6, 2022

(54) LARGE SCALE PURIFICATION OF CASTANOSPERMINE

(71) Applicant: FLORIDA STATE UNIVERSITY RESEARCH FOUNDATION, INC., Tallahassee, FL (US)

(72) Inventors: Eric Holmes, Tallahassee, FL (US); Gary Ostrander, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 83 days.

(21) Appl. No.: 17/303,698

(22) Filed: Jun. 4, 2021

(65) Prior Publication Data

US 2021/0380583 A1    Dec. 9, 2021

Related U.S. Application Data

(60) Provisional application No. 63/034,747, filed on Jun. 4, 2020.

(51) Int. Cl.
*C07D 471/04*    (2006.01)

(52) U.S. Cl.
CPC ................... *C07D 471/04* (2013.01)

(58) Field of Classification Search
CPC ..................................... C07D 471/04
USPC ........................................... 546/183
See application file for complete search history.

(56) References Cited

PUBLICATIONS

Fleet et al., Tetrahedron Letters (1988), vol. 29(29), pp. 3603-3606.*

* cited by examiner

*Primary Examiner* — Niloofar Rahmani
(74) *Attorney, Agent, or Firm* — Thomas Horstemeyer, LLP

(57) ABSTRACT

The invention concerns a scalable, large-scale castanospermine preparation method that yields levels of purity greater than 98% from castanospermine-containing plant sources, such as *Castanospermum australe* seed material.

20 Claims, 1 Drawing Sheet

LARGE SCALE PURIFICATION OF CASTANOSPERMINE

CROSS-REFERENCE TO RELATED APPLICATION

The present application claims the benefit of U.S. Provisional Application Ser. No. 63/034,747, filed Jun. 4, 2020, which is hereby incorporated by reference herein in its entirety, including any figures, tables, nucleic acid sequences, amino acid sequences, or drawings.

BACKGROUND OF THE INVENTION

Castanospermine is an alkaloid produced by the *Castanospermum australe* tree and is enriched in its seeds. Castanospermine is an alpha-glucosidase inhibitor which inhibits glycoprotein processing in mammalian cells by preventing removal of 3-glucose residues linked to a high mannose core structure. This Glc3Man9GlcNAc2 structure is transferred enblock to an N-linked site in a glycoprotein (N-X-S/T, where N is glutamine, X is any amino acid except Proline, followed by either a Serine or Threonine). After transfer, alpha-glucosidase removes the three glucose residues and allowing further processing by multiple mannosidases to reach a core capable of conversion to the complex type oligosaccharide structure catalyzed by multiple glycosyltransferases that is found on most glycoproteins. By inhibiting the initial step, castanospermine prevents glycoprotein processing to yield the complex-type structure. This processing occurs in the endoplasmic reticulum and is very often required in order for proper protein folding to occur and yield a physiologically active protein.

This activity of castanospermine has an antiviral effect on many viruses given that many viruses have coat glycoproteins and it has been shown that in many instances misfolded proteins lacking activity occur with castanospermine treatment. Thus, castanospermine is a potential anti-viral therapeutic (Whitby K et al., *J Virol.*, July 2005, 79(14):8698-8706; U.S. Pat. No. 10,561,642).

An analytical, small-scale method for producing castanospermine is known (Hohenschutz L et al., 1981, *Phytochemistry*, 20:811-814). To purify large quantities of castanospermine needed for large-scale therapeutic use, a preparation method tailored to the needs of large-scale production, would be advantageous.

BRIEF SUMMARY OF THE INVENTION

The method of the invention is a scalable, large-scale castanospermine preparation method. The preparation method differs in significant ways from methods for small-scale analytical isolation of castanospermine and is capable of yielding levels of purity greater than 98%.

One aspect of the invention is a method for preparing castanospermine, comprising:

(a) separating a liquid fraction comprising castanospermine from solid plant material, such as *Castanospermum australe* seed material;

(b) purifying the castanospermine in the liquid fraction from (a) by: (i) mixing the liquid fraction with an ion exchange medium (e.g., ion exchange resin or ion exchange polymer) under conditions that allow castanospermine in the liquid fraction to be bound to the resin, or (ii) column chromatography using a chromatography medium;

(c) eluting the castanospermine from the ion exchange medium of (b)(i) or chromatography medium of (b)(ii) to produce an eluate; and (d) purifying the castanospermine in the eluate of (c) by mixing the eluate with an ion exchange medium (e.g., ion exchange resin or ion exchange polymer) under conditions that allow castanospermine in the eluate to be bound to the ion exchange medium, and eluting the castanospermine.

DETAILED DESCRIPTION OF THE INVENTION

Figure 1:
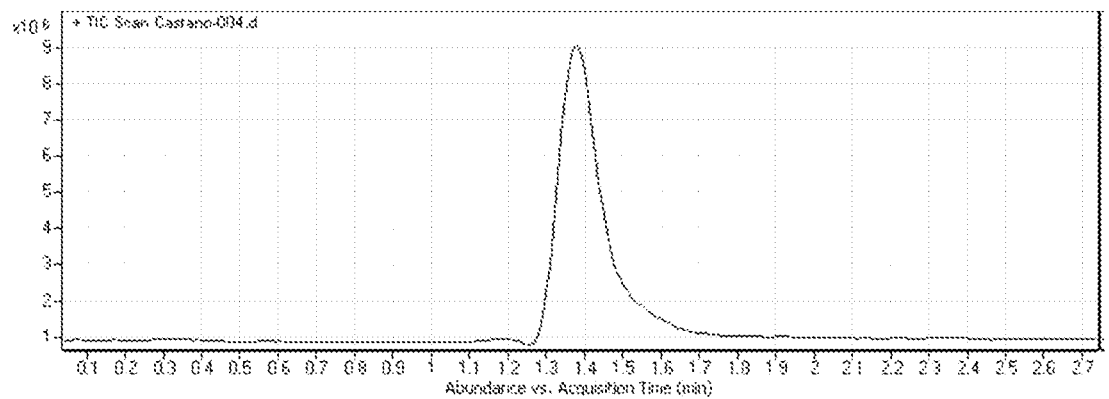
FIG. 1 shows a chromatogram from typical conditions for LC/MS analysis of castanospermine (see Example). The purity of castanospermine can be assessed based upon the chromatogram.

The invention concerns a method for preparing castanospermine, comprising:

(a) separating a liquid fraction comprising castanospermine from solid plant material, such as *Castanospermum australe* seed material;

(b) purifying the castanospermine in the liquid fraction from (a) by: (i) mixing the liquid fraction with an ion exchange medium (e.g., ion exchange resin or ion exchange polymer) under conditions that allow castanospermine in the liquid fraction to be bound to the resin, or (ii) column chromatography using a chromatography medium;

(c) eluting the castanospermine from the ion exchange medium of (b)(i) or chromatography medium of (b)(ii) to produce an eluate; and (d) purifying the castanospermine in the eluate of (c) by mixing the eluate with an ion exchange medium (e.g., ion exchange resin or ion exchange polymer) under conditions that allow castanospermine in the eluate to be bound to the ion exchange medium, and eluting the castanospermine.

Preparation of Raw Seed Material

The plant material can be prepared by cutting, breaking up, and/or grinding, producing ground particles, preferably of a size no larger than about 2 millimeters in diameter. Thus, the plant material may be "processed" into pieces or particulate form. In some embodiments, the plant material is homogenized. Any homogenization method may be used that is appropriate for the scale of the material being processed.

Any castanospermine-containing plant material may potentially be utilized as source material for the preparation method, from one or more castanospermine-containing plants, and from one or more castanospermine-containing parts of the plant(s), such as seeds, stem, leaf, pod, etc. If seeds having seed cases are used, the seed cases are typically removed, leaving just the seed, as described in the Example.

Examples of castanospermine-containing plants that may be used include *Castanospermum australe*, as was used in the Example, and *Alexa* spp. Examples of castanospermine-containing *Alexa* species include *A. canaracunensis* Pittier, *A. cowanii* Yakovlev, *A. grandiflora* Ducke, *A. herminiana*

Ramirez, *A. imperatricis* (R.H. Schomb.) Baill., *A. leiopetala* Sandwith, *A. superba* RS Cowan, and *A. wachenheimii* Benoist.

In some embodiments, the plant material comprises one or more parts of *C. australe*, such as *C. australe* seeds or leaf. In some embodiments, the plant material comprises *C. australe* seeds lacking seed cases.

Further details concerning preparation of the solid material are provided in the "Grinding seeds" section of the Example. It should be understood that, although the Example refers to *C. australe* seeds, any other castanospermine-containing plant species and plant parts may potentially be substituted.

Separation of Liquid Fraction

Once the plant material is processed (i.e., broken up, cut, and/or ground into pieces particulate matter, and preferably homogenized), the method comprises separating a liquid fraction containing castanospermine. The separating step (a) includes an extraction, such as an ethanol extraction, to obtain a liquid fraction containing castanospermine, and solid material. Various ethanol concentrations may be used for the ethanol extraction, provided the final ethanol concentration is sufficient to precipitate the starch from the plant material. For example, the final ethanol concentration may be at least about 60%, depending upon the amount of water in the plant material (e.g., the amount of water in seeds). In some embodiments, the final ethanol concentration is in the range of 70% to 75%. In some embodiments, the separating step (a) comprises: (i) allowing the solid material to settle out and placing (e.g., pumping) most of the liquid (first recovered fraction) into a container (e.g., a vat or other vessel) followed by filtration or centrifugation of the remaining material to remove the rest of the liquid fraction (second recovered fraction) and combining the second recovered fraction with the first recovered fraction; or (ii) directly separating the liquid fraction from the solid material using a continuous process such as centrifugation or filtration.

Typically, the solid material recovered from the first extraction will be a moist cake. Optionally, the separating step (a) is repeated on the solid material one or more times, pooling the liquid fractions obtained from each separation. Depending upon the specific separation method used to obtain the liquid fraction, there may be very fine particles remaining in the liquid fraction. This will settle out and can be removed from the liquid prior to purifying step (b), or at a later step. Further details concerning preparation for the separation step are provided in "1. Grinding seeds" and "2. Homogenizing ground seed meal" sections of the Example.

Optional Alternative Heat Treatment

This optional heat treatment has the advantage of not using ethanol for extraction from the plant material (e.g., seeds), and would just be utilized for the extraction phase.

The procedure involves heating raw castanospermine-containing plant material (e.g., *Castanospermum* seeds) to an internal temperature sufficient to denature starch and other components (e.g., about 63 to about 77 degrees C.). Preferably, the plant material is then to cool, e.g., to room temperature or ambient temperature. This heat treatment will render the starch and other components mostly insoluble in water (by contrast, when ethanol is used in extraction fluid, it is largely there to precipitate starch and other components so they can be filtered away more easily). Castanospermine is stable to this heat treatment.

The cooled plant material (e.g., seeds) can then be ground or cut up to yield pieces and/or particles about 2 to 4 mm in diameter and placed in water (e.g., deionized water). This mixture can either be stirred to keep the seed pieces and/or particles suspended or more aggressively mixed to break the pieces up, for example, in a blender. The more gentle stirring will require more extraction time for the castanospermine to leach out into the water, for example, overnight but will leave solid residue that will settle out on its own and not require filtration or centrifugation to obtain a clear or slightly turbid aqueous solution containing extracted castanospermine. More aggressive mixing or blending will not require an extensive extraction time for the castanospermine to become dissolved in water but, after allowing solid residue to settle, the aqueous solution may have considerable particulate material to filter or centrifuge out. The solid residue can optionally be re-extracted with additional deionized water.

From either option the pooled aqueous solution can then be mixed with an ion exchange medium (such as a Dowex 50 H+ form ion exchange resin or other strongly acidic cation exchange resin), either batch-wise with stirring, or poured into a chromatography column, as described below. After mixing with the ion exchange medium or passing through the chromatography column with chromatography medium, the aqueous solution is discarded and the resin extensively washed with water (e.g., deionized water) and eluted with 2N $NH_4OH$ as described elsewhere. Subsequent steps are the same as if ethanol had been used for the initial extraction.

Purifying Castanospermine in Liquid Fraction

The initial purifying step (b) comprises purifying the castanospermine in the liquid fraction from (a) by: (i) mixing the liquid fraction with an ion exchange medium (e.g., ion exchange polymer or ion exchange resin, such as DOWEX-50 $H^+$ form ion exchange resin or other strongly acidic cation exchange resin) under conditions that allow castanospermine in the liquid fraction to be bound to the resin, or (ii) column chromatography using a chromatography medium. In some embodiments, the ion exchange medium of step (b) comprises ion exchange beads.

Strongly acidic mediums such as DOWEX-50 $H^+$ contain exchangeable H+ cations which give the resins the ability to behave as insoluble, but very reactive acids. Not only can these resins be used to exchange the H+ ion for the cations of a salt in solution, effectively "salt splitting" and forming the acid of the salt involved in solution, but they can be used in place of soluble acid in many catalytic reactions. DOWEX cation resins include standard gel products such as DOWEX HCR-S, DOWEX HCRW2, DOWEX HGR and DOWEX HGR-W2, macroporous products such as DOWEX M-31, uniform particle size products such as DOWEX G-26, and dried catalysts such as DOWEX DR 2030.

Optionally, the method includes sampling the mixture after mixing for a duration of time in (b)(i), and measuring the amount of castanospermine remaining in the liquid phase (such as by liquid chromatography mass spectrometry (LC/MS)).

Further details concerning the initial purifying step of (b) are provided in "3. Treatment with Dowex-50$H^+$ form" section of the Example.

Elution of Castanospermine

In step (c), the elution of castanospermine from the ion exchange medium of (b)(i) or chromatography medium of (b)(ii) in the initial purification step of (b) is carried out in an elution vessel, such as a column, to produce an eluate (one or more castanospermine-containing eluted fractions). Ammonium hydroxide ($NH_4OH$) or other suitable elution solvent may be used. As the elution solvent moves through the elution vessel, the heat of neutralization will create warming, which allows the progress of the elution to be easily monitored. For example, heat sensitive tape affixed to the side of the vessel may be used. The castanospermine elutes from vessel in the region of the warming front and fractions can be collected of any practical size. Alternatively, it is possible to carry out the elution step of (c) in a batchwise fashion, and separating the castanospermine-containing supernatant fraction from the ion exchange medium or chromatography medium using any suitable method.

Optionally, the method includes assaying the amount of castanospermine in the eluted fractions (e.g., by LC/MS) and pooling those fractions with desired high amounts of castanospermine present in order to minimize the amount of impurities carried to the next step.

Optionally, the method further comprises removing residual solvent after the elution of (c) and before the purifying step of (d). Because it is possible that some elution solvent (e.g., $NH_4OH$) could interfere with the efficient castanospermine binding in the subsequent purification step of (d), residual solvent can be removed by any suitable method capable of removing the residual solvent, such as drying or concentration. For example, a rotary evaporator may be used for concentration of solvent.

Optionally, the ion exchange medium may be regenerated back to the H+ form, and can be used one or more times for absorption of castanospermine from additional liquid extracts of seed material from step (a) following the same procedures described above.

Further details concerning the elution step of (c) are provided in the "4. Elution of castanospermine from Dowex 50 $H^+$ form" section and in the "5. Preparation of the castanospermine containing Dowex 50 H+ form eluted fractions for subsequent steps" section of the Example.

Purifying Castanospermine in Eluate

The purification step of (d) comprises purifying the castanospermine in the eluate of (c) by mixing the eluate with an ion exchange medium (e.g., ion exchange resin or ion exchange polymer) under conditions that allow castanospermine in the eluate to be bound to the ion exchange medium, and eluting the castanospermine. This step can be carried out batch-wise, or over a column or other vessel. Preferably, the ion exchange medium of the purifying step of (d) comprises a pyridinium ion form resin, wherein castanospermine is exchanged with the pyridinium ion, resulting in castanospermine bound to the resin and pyridine released into solution. The castanospermine may be eluted in the purifying step (d) using an elution solvent, such as pyridine in deionized water, or $NH_4OH$.

The purity of castanospermine that may be achieved using the purifying step of (d) can be least about 95% if the castanospermine is eluted by a column or other vessel, or about 90% to about 95% if the castanospermine is eluted batch-wise.

Further details concerning the purification step of (d) are provided in the "6. Purification on Dowex 50 pyridinium ion form resin" section of the Example.

Optionally, the purification step of (d) further comprises further purifying the eluate. The step can include: (i) repeating the purifying step of (d) on the eluate, or (ii) recrystallizing the castanospermine enriched crystals in the eluate of step (d) with a solvent, such as ethanol, optionally sonicating, placing the solution at reduced temperature to stimulate crystal formation, for harvesting and drying.

Further details concerning the further purification step of (d) are provided in the "7. Further purification of castanospermine" section of the Example.

Optionally, the ion exchange medium of step (d) can be regenerated one or more times for repeated use. Details concerning the regeneration step are provided in the "8. Regeneration of Dowex 50 resin used in castanospermine purification" section of the Example.

The method of the invention may further comprise detecting the presence of castanospermine, or measuring the amount of castanospermine (e.g., to assess purity), in the product of one or more of steps (a), (b), (c), or (d). In some embodiments, liquid chromatography mass spectrometry (LC/MS) is utilized. Further details concerning LC/MS are provided in the "9. LC/MS assay for castanospermine" section of the Example.

As is well-known in the art, the steps in a cycle of chromatography can differ depending on the chromatography resin, the buffers used to perform each step in the cycle, and the biophysical characteristics of a target compound, such as castanospermine. For example, an affinity chromatography column can include the steps of loading an affinity chromatography column with a fluid including castanospermine, washing the column to remove unwanted material, eluting the castanospermine bound to the column, and re-equilibrating the column. A cycle of chromatography, using a cationic and/or anionic exchange chromatography column, where the castanospermine binds to the chromatography resin in the loading step, can include the steps of loading the column with a fluid including the target compound, washing the column to remove unwanted material, eluting the target compound to the column, and re-equilibrating the column. In other examples, a cycle of chromatography using a cationic and/or anionic exchange chromatography column, where unwanted material binds to the chromatography resin during the loading step, while the target compound does not, can include the steps of loading the column with a fluid including the target compound, collecting the compound in the flow-through, and re-equilibrating the column. As is well-known in the art, any of the single steps in a chromatography cycle can include a single buffer or multiple buffers (e.g., two or more buffers), and one or more of any of the single steps in a chromatography cycle can include a buffer gradient. Any of the combination of various well-known aspects of a single cycle of chromatography can be used in these methods in any combination, e.g., different chromatography resin(s), flow-rate(s), buffer(s), void volume(s) of the column, bed volume(s) of the column, volume(s) of buffer used in each step, volume(s) of the fluid including the target protein, and the number and types of buffer(s) used in each step.

The columns used for the column chromatography and elution can be any suitable vessel of any cross-sectional shape that allows loading from one end (e.g., top) and outflow from the other end (e.g., bottom). Typically, the column is tubular, having a cylindrical, near cylindrical, or ellipsoidal shape. (e.g., a cylinder, near cylindrical shape, or ellipsoidal shape).

Optionally, the castanospermine preparation method further comprises chemically modifying the resulting castanospermine to make a derivative of castanospermine.

Optionally, as with other active pharmaceutical ingredients, the castanospermine or castanospermine derivative may be formulated as a pharmaceutically acceptable salt to achieve desirable formulation properties (Gupta D et al., "Salts of Therapeutic Agents: Chemical, Physiochemical, and Biological Considerations," *Molecules*, 2018, 23:1719;

Makary, P., "Principles of Salt Formation", *UK Journal of Pharmaceutical and Biosciences,* 2014, 2(4):01-04).

EXEMPLIFIED EMBODIMENTS

Embodiment 1

A method for preparing castanospermine, comprising:
(a) separating a liquid fraction comprising castanospermine from castanospermine-containing solid plant material;
(b) purifying the castanospermine in the liquid fraction from (a) by: (i) mixing the liquid fraction with an ion exchange medium (e.g., ion exchange resin or ion exchange polymer) under conditions that allow castanospermine in the liquid fraction to be bound to the resin, or (ii) column chromatography using a chromatography medium;
(c) eluting the castanospermine from the ion exchange medium of (b)(i) or chromatography medium of (b)(ii) to produce an eluate; and
(d) purifying the castanospermine in the eluate of (c) by mixing the eluate with an ion exchange medium (e.g., ion exchange resin or ion exchange polymer) under conditions that allow castanospermine in the eluate to be bound to the ion exchange medium, and eluting the castanospermine.

Embodiment 2

The method of embodiment 1, wherein the castanospermine-containing plant material comprises castanospermine-containing plant seed material, and wherein the castanospermine-containing plant seed material is prepared for said separating by grinding seeds lacking seed cases, producing ground particles of a size no larger than about 2 millimeters in diameter, and preferably homogenized.

Embodiment 3

The method of embodiment 1, wherein the castanospermine-containing solid plant material is any castanospermine-containing part or parts of *Castanospermum australe, Alexa* spp., or a combination thereof.

Embodiment 4

The method of embodiment 1, wherein the castanospermine-containing solid plant material comprises or consists of solid *Castanospermum australe* seed material.

Embodiment 5

The method of embodiment 4, wherein *C. australe* seed material is prepared by grinding *C. australe* seeds lacking seed cases, producing ground particles of a size no larger than about 2 millimeters in diameter.

Embodiment 6

The method of any preceding embodiment, wherein said separating of step (a) includes an ethanol extraction; or wherein said separating of step (a) includes a heat treatment comprising heating the castanospermine-containing solid plant material (e.g., seeds) sufficiently to denature starch within the plant material (e.g., about 63 to 77 degrees C.), allowing the heat-treated plant material to cool, grinding and/or cutting the cooled plant material, and carrying out water extraction on the plant material to obtain the liquid fraction comprising castanospermine.

Embodiment 7

The method of embodiment 1, wherein said separating of step (a) comprises: (i) allowing the solid material to settle out and placing (e.g., pumping) most of the liquid (first recovered fraction) into a container (e.g., a vat or other vessel) followed by filtration or centrifugation of the remaining material to remove the rest of the liquid fraction (second recovered fraction) and combining the second recovered fraction with the first recovered fraction; or (ii) directly separating the liquid fraction from the solid material using a continuous process such as centrifugation or filtration.

Embodiment 8

The method of any preceding embodiment, wherein the separating of step (a) is repeated one or more times, pooling the obtained liquid fractions from each separation.

Embodiment 9

The method of any preceding embodiment, wherein the ion exchange medium of step (b) is an acidic cation exchange medium (e.g., DOWEX-50 $H^+$).

Embodiment 10

The method of any preceding embodiment, wherein the ion exchange medium of step (b) comprises ion exchange beads.

Embodiment 11

The method of any preceding embodiment, further comprising sampling the mixture after mixing for a duration of time in (b)(i), and measuring the amount of castanospermine remaining in the liquid phase (such as by liquid chromatography mass spectrometry (LC/MS)).

Embodiment 12

The method of any preceding embodiment, further comprising assaying the amount of castanospermine in the eluted fractions (e.g., by LC/MS) in said eluting step (c) and pooling those fractions with desired high amounts of castanospermine present in order to minimize the amount of impurities carried to the next step.

Embodiment 13

The method of any preceding embodiment, wherein the solvent used for said eluting step of (c) is ammonium hydroxide ($NH_4OH$).

Embodiment 14

The method of any preceding embodiment, further comprising removing residual solvent after said eluting of step (c) and before said purifying of (d).

Embodiment 15

The method of any preceding embodiment, wherein said purifying step of (d) is carried out batch-wise, or over a column or other vessel.

Embodiment 16

The method of embodiment 1, wherein the ion exchange medium of said purifying step of (d) comprises a pyridinium ion form resin, wherein castanospermine is exchanged with the pyridinium ion, resulting in castanospermine bound to the resin and pyridine released into solution.

Embodiment 17

The method of any preceding embodiment, wherein castanospermine is eluted in said purifying step (d) using an elution solvent comprising: pyridine in deionized water, or ammonium hydroxide ($NH_4OH$).

Embodiment 18

The method of any preceding embodiment, wherein the purity of castanospermine after said purifying step of (d) is at least about 95% if the castanospermine is eluted by a column or other vessel, or about 90% to about 95% if the castanospermine is eluted batch-wise.

Embodiment 19

The method of any preceding embodiment, comprising further purifying eluate of step (d).

Embodiment 20

The method of embodiment 19, wherein said further purifying comprises: (i) repeating the purifying step of (d) on the eluate, or (ii) recrystallizing the castanospermine enriched crystals in the eluate of step (d) with a solvent, such as ethanol, optionally sonicating, placing the solution at reduced temperature to stimulate crystal formation, for harvesting and drying.

Embodiment 21

The method of any preceding embodiment, further comprising regenerating the ion exchange medium of step (d).

Embodiment 22

The method of any preceding embodiment, further comprising measuring the amount of castanospermine in the product of one or more of steps (a), (b), (c), or (d).

Embodiment 23

The method of embodiment 22, wherein said measuring is conducted by liquid chromatography mass spectrometry (LC/MS).

Definitions

The term "a," "an," "the" and similar terms used in the context of the present invention (especially in the context of the claims) are to be construed to cover both the singular and plural unless otherwise indicated herein or clearly contradicted by the context. For example, the term "compound" includes a singular compound and a plurality of compound unless specified to the contrary. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, a "derivative" or "pharmaceutically active derivative" refers to any compound that upon administration to the recipient, is capable of providing directly or indirectly, the activity of castanospermine (e.g., anti-viral activity, alpha-glucosidase inhibitory activity, such as inhibition of alpha-glucosidase I). The term "indirectly" also encompasses "prodrugs" which may be converted to the active form of the drug, e.g., via endogenous enzymes or metabolism (biotransformation). The prodrug is a derivative of the castanospermine and presenting desired activity (e.g., anti-viral activity, alpha-glucosidase inhibitory activity) that has a chemically or metabolically decomposable group, and a compound that may be converted into a pharmaceutically active compound according to the invention in vivo by solvolysis under physiological conditions. The prodrug is converted into castanospermine by a reaction with an enzyme, gastric acid or the like under a physiological condition in the living body, e.g., by oxidation, reduction, hydrolysis or the like, each of which is carried out enzymatically. These compounds can be produced from castanospermine according to well-known methods. The term "indirectly" also encompasses metabolites of compounds according to the invention. Chemical reactions, reactants, and reagents useful for making derivatives can be found, for example, in *March's Advanced Organic Chemistry*, 7$^{th}$ edition, 2013, Michael B. Smith, which is incorporated herein by reference in its entirety.

More specifically, the term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals*, 2009, 2(3):77-81, which is incorporated by reference herein in its entirety).

The term "metabolite" refers to all molecules derived from castanospermine in a cell or organism, preferably mammal. Pharmaceutically active metabolites of the compounds of the invention may be administered to a subject or contacted with a cell in vitro or in vivo.

The phrase "pharmaceutically acceptable" indicates that the substance or composition must be compatible chemically and/or toxicologically, with the other ingredients comprising a formulation, and/or the mammal being treated therewith.

Pharmaceutical formulations include "pharmaceutically acceptable" and "physiologically acceptable" carriers, diluents or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

The phrase "effective amount" means an amount of an agent, such as castanospermine or a derivative thereof, that (i) treats or prevents the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein. Castanospermine has been shown to inhibit infection by certain viruses in vitro and/or in vivo (Whitby K et al., *J Virol.*, July 2005, 79(14):8698-8706; U.S. Pat. No. 10,561,642). Thus, in the context of castanospermine or a derivative thereof, an "effective amount" may also mean an amount that (iv) inhibits viral infection in vitro and/or in vivo (e.g., flavivirus infection such as Dengue virus), or (v) inhibits one or more types of glucosidases in vitro or in vivo.

Castanospermine, derivatives, and pharmaceutically acceptable salts of castanospermine and derivatives produced using the method of the invention, and compositions comprising them, can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention.

In general, the compositions can be formulated such that an effective amount of the castanospermine or derivative thereof is combined with a suitable carrier in order to facilitate effective administration of the composition. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also may include conventional pharmaceutically acceptable carriers and diluents which are known to those skilled in the art. Examples of carriers or diluents for use with the castanospermine and its derivatives include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of castanospermine and derivatives thereof can also comprise suspension agents, protectants, lubricants, buffers, preservatives, and stabilizers. To provide for the administration of such dosages for therapeutic treatment, pharmaceutical compositions of the invention may comprise between about 0.1% and 45%, and especially, 1 and 15% by weight of the total of the castanospermine, and optionally other active ingredients, based on the weight of the total composition including carrier or diluent.

All patents, patent applications, provisional applications, and publications referred to or cited herein are incorporated by reference in their entirety, including all figures and tables, to the extent they are not inconsistent with the explicit teachings of this specification.

Following is an example that illustrates procedures for practicing the invention. These examples should not be construed as limiting. All percentages are by weight and all solvent mixture proportions are by volume unless otherwise noted.

Example—Large-Scale Purification of Castanospermine from *Castanospermum australe* Seeds This method can be adjusted to accommodate any needed scale of the production process.

1) Grinding Seeds.

Seed cases of the seeds of the *Castanospermum australe* tree are removed and discarded, leaving just the seed (generally oval shaped at about 3-5 cm in diameter and 2 cm thick). The seeds are ground using any method suitable for the scale of purification being conducted. Multiple passes through the grinder or grinding process can be used to generate a fine moist meal. The smaller the size of the ground particles the better and should be no larger than about 2 mm in size.

2) Homogenizing Ground Seed Meal.

Ground seed meal is mixed with 1-2 volumes (v/v) of 75% ethanol (prepared by mixing 95% EtOH with deionized water and adjusting the EtOH concentration to 75% by use of a hydrometer) and vigorously homogenized for 10-12 minutes. Other ethanol concentrations may be used for extraction, provided the final ethanol concentration is sufficient to precipitate the starch from the plant material. Any suitable homogenization method can be used based upon the scale being processed. The intent is to thoroughly extract the seed meal and reduce the size of the particles to roughly the size of ground coffee.

Once the homogenization step is completed the liquid is removed from the solid material. This can be accomplished in a number of ways to include: a) allowing the solid material to settle out and pump most of the liquid into a large vat or vessel followed by filtration by any suitable means or centrifugation of the remaining material to remove the rest of the liquid fraction and is combined the liquid recovered earlier; b) separating the liquid fraction from the solid material directly by a continuous process such as centrifugation or filtration; or c) any other means of separating the liquid fraction from the solid material suitable for use in the scale of the process being used.

After completion of the first extraction step, the recovered solid material will be a moist cake. This can optionally be extracted a second time using an additional 2-3 volumes (v/v) of 75% ethanol and the extraction process repeated. In the end, all liquid fractions can be pooled and processed in the next step (purification). The twice extracted solid material can be discarded. While a third extraction will likely yield additional castanospermine; it is not cost-effective.

Optional Heat Treatment as Alternative to 1) and 2), Above:

This optional heat treatment has the advantage of not using ethanol for extraction from the seeds, and would just be utilized for the extraction phase.

The procedure involves heating raw *Castanospermum* seeds to an internal temperature sufficient to denature starch and other components (e.g., about 63 to about 77 degrees C.) and allowing them to cool. This heat treatment will render the starch and other components mostly insoluble in water (by contrast, ethanol in extraction fluid is largely there to precipitate starch and other components so they can be filtered away more easily). Castanospermine is stable to this heat treatment.

The cooled seeds are then ground or cut up to yield pieces about 2 to 4 mm in diameter and placed in deionized water. This mixture can either be stirred to keep the seed pieces suspended or more aggressively mixed to break the pieces up, for example, in a blender. The more gentle stirring will require more extraction time for the castanospermine to leach out into the water, for example, overnight but will leave solid residue that will settle out on its own and not require filtration or centrifugation to obtain a clear or slightly turbid aqueous solution containing extracted castanospermine. More aggressive mixing or blending will not require an extensive extraction time for the castanospermine to become dissolved in water but, after allowing solid residue to settle, the aqueous solution may have considerable particulate material to filter or centrifuge out. The solid residue can optionally be re-extracted with additional deionized water.

From either option the pooled aqueous solution can then be mixed with an ion exchange resin such as Dowex 50 H+ form, either batch wise with stirring or poured into a column, as described in 3), below. After mixing with the resin or passing through the resin, the aqueous solution is discarded and the resin extensively washed with deionized water and eluted with an elution solvent (e.g., 2N $NH_4OH$) as described elsewhere. Subsequent steps are the same as if ethanol had been used for the initial extraction.

3) Treatment with Dowex-50 $H^+$ Form.

Batchwise Treatment:

Depending on the separation method used to obtain the liquid fraction there may be very fine particles or "flour" remaining in the liquid fraction. This will settle out and can easily be removed from the clear liquid prior to the next step. However, it is not critical or necessary to remove the fine particles as they will be eliminated in a later step.

The liquid is mixed with Dowex-50 $H^+$ form ion exchange resin (or other similar strongly acidic cation exchange resin), 25-50 mesh or other suitable size of resin (very small resin particles, 100 mesh or smaller will be inconvenient in subsequent steps and lead to losses of resin and castanospermine) in approximate proportions of 1 liter of packed resin plus the liquid derived from the extraction of 3.5 Kg of ground seed meal. This is then placed in a suitably sized container and stirred under adequate conditions which allow the resin to remain suspended in the liquid and not settle to the bottom. This proportion of resin to liquid extract necessary will vary depending on the castanospermine content of the seeds being extracted. Generally the castanospermine content of the raw seeds is about 0.5% to 1% by weight. Accordingly, the amount of resin and liquid extract appropriate for a given batch of seeds can be optimized by sampling the liquid after stirring for ½ to 1 hour and testing the amount of castanospermine remaining in the liquid phase by LC/MS (see under "LC/MS assay" below).

Based on this, an optimal amount of liquid extract to resin ratio can be determined that is capable of yielding >90-95% of the castanospermine bound to the resin and the period of time the mixture must be stirred to achieve that result. This proportion should be relevant for any subsequent extractions with a given batch of seeds. This is helpful to begin reducing the scale of the process in subsequent steps.

After the castanospermine has been absorbed on to the resin, the resin can be allowed to settle to the bottom of the vessel being used and the liquid fraction poured or pumped off. This liquid, generally about 60% EtOH, can be recycled by distillation to obtain clear, colorless EtOH and used again after adjusting the EtOH concentration with deionized water to 75% through the use of a hydrometer.

The resin, which may be turbid from the seed residue and "flour", is washed extensively with deionized water until the liquid becomes clear and lacks turbidity. Washing is done by thorough stirring of the resin and suspending it in deionized water, allowing the resin to settle, and removing the water by any suitable method depending on scale. It is important to do this quickly to minimize the amount of seed residue that is able to settle with the resin before removal of the water wash. Once the resin is thoroughly washed and no turbidity remains in the water wash, the resin can be optionally transferred to a vessel capable of draining from the bottom and being able to be filled from the top. It can be an open vessel or sealed vessel that allows fluid to flow through the resin bed either by gravity or by pumping. The size and shape of the vessel to be used is based upon the volume needs for the amount of resin being used. A column containing either straight or tapered sides is ideal. The bottom of the column or other vessel must have a porous barrier that will not allow the resin to pass through while allowing the eluting liquid to freely flow. To monitor progress of the elution step it is convenient to affix some heat sensitive tape (for example which changes color when warmed) to the side of the vessel containing the resin.

Column Treatment:

An alternate method for initial purification of 75% ethanol extracted seed meal is via column chromatography depending on scale, available equipment, and individual preferences.

To apply column chromatography the biggest difference from the batchwise method is that all of the particulate and insoluble "flour" from the seed should be completely removed prior to loading the column. This material can otherwise clog the column and severely reduce or stop the flow rate. Removal can be done in a variety of ways or steps. The extract can be allowed to stand for an adequate period of time for this insoluble material to settle to the bottom of the container. And/or, the extract can be either filtered or centrifuged, for example in a continuous flow centrifuge, to yield clarified extract capable of being loaded onto the resin which is either in a column or other suitable vessel which allows loading from one end (e.g. top) and outflow from the other end (e.g. bottom). The size of the column and amount of resin to use is based on the scale of the preparation and can be adjusted as described above to optimize the amount of seed meal that can be processed at a time. The column is loaded and washed extensively with deionized water until the effluent is clear and the conductivity of the mixture is similar to deionized water indicating any unbound contaminants have been eliminated. The column is then eluted and the castanospermine is further processed as described below.

4) Elution of Castanospermine from Dowex 50 $H^+$ Form.

After transferring the batch-washed resin to an elution vessel (as necessary), the resin is further washed with water to remove any additional turbidity that may remain. It is then eluted using 2M $NH_4OH$. Depending on the size and dimensions of the elution vessel being used, it is often desirable to place a porous barrier such as filter paper or the like on the top of the resin bed to minimize disruption of the resin bed as the elution solvent is added to the vessel. As the $NH_4OH$ goes down the column the heat of neutralization will create warming allowing the progress of the elution to easily be monitored. After the warming front reaches about half way down the vessel, fractions of any practical size can be collected. The castanospermine elutes from the column in the region of the warming front and fractions just prior to it flowing from the column. This can be conveniently monitored by heat sensitive tape affixed to the side of the elution vessel. Once the warming front has passed through the column an odor of ammonia will be present and all of the castanospermine is off the column. Additional $NH_4OH$ can be passed over the resin to elute general impurities. It is possible to assay the amount of castanospermine in the eluted fractions by LC/MS and pool just those fractions with high amounts of castanospermine present to minimize the amount of impurities carried along to the next step.

The resin, after eluting with a desired amount of additional 2 M $NH_4OH$ is then washed extensively with deionized water followed by treatment with 2 N HCl or 2 M $H_2SO_4$ to convert the resin back to the $H^+$ form. Adequate acid is put over the resin until the pH eluting from the bottom is strongly acidic. At that point the resin is washed extensively with water until the pH is no longer strongly acidic (it may go to pH 5 or so).

It is possible to alternately do all elution steps of the Dowex 50 $H^+$ form resin using 2N $NH_4OH$ in a batchwise fashion and separating the castanospermine containing supernatant fraction from the resin using a convenient method.

Once the Dowex 50 resin has been converted back to the $H^+$ form and extensively water washed (for a detailed procedure see below under "Regeneration of Dowex 50 resin"), it can be used again (and again) for absorption of castanospermine from additional liquid ethanol extract of seed meal following the same procedures described above.

5) Preparation of the Castanospermine Containing Dowex 50 $H^+$ Form Eluted Fractions for Subsequent Steps.

The fractions from the above step which contain the desired levels of castanospermine (which can be determined using LC/MS analysis) are pooled. It is possible that some $NH_4OH$ may be present which could interfere with efficient castanospermine binding in the next purification step. Residual $NH_4OH$ can be removed by any means capable of evaporating the residual $NH_4OH$. One method is via concentration using a rotary evaporator. It is only necessary to treat (or concentrate) the pooled fractions until all odor from $NH_4OH$ has been removed. During rotary evaporation (or any other method of concentration or removal of $NH_4OH$) it is possible to heat the pooled fractions to at least as much as 80° C. without harming (degrading) the castanospermine.

6) Purification on Dowex 50 Pyridinium Ion Form Resin.

The castanospermine containing concentrate from the Dowex 50 $H^+$ resin elution is then mixed (either batchwise or over a column or other vessel containing a means for liquids to flow from the top and outflow through the bottom) with Dowex 50 resin in the pyridinium ion form (again, 25-50 mesh is suitable). This resin forms a separate batch of Dowex 50 resin used only for this purpose and is kept separate from the resin used in the first step. Varying amounts of resin can be used based upon the scale of the purification being conducted. An amount of resin to use can be estimated based upon the total exchange capacity of the resin and estimates of the amount of castanospermine present in the eluted fractions of the previous step. This amount can be roughly determined by LC/MS assays of castanospermine. The resin can be prepared by passing pyridine in deionized water (for example, 2 M pyridine) over Dowex 50 $H^+$ form resin in a column or similar vessel, or by adding it to the resin batchwise. Adequate pyridine is passed over the resin in a column or is mixed with the resin batchwise until an odor of pyridine is apparent in the column outflow or in the liquid portion of the batchwise treatment. The resin is then washed extensively with deionized water until the residual pyridine odor is not apparent or is very low. The resin can then be used in the next step.

Pooled fractions that eluted with 2N $NH_4OH$ from the initial Dowex 50 $H^+$ form resin (conducted either batchwise or using a column or vessel capable of allowing elution solvent to flow through the resin and out the bottom), after removal of excess $NH_4OH$, are contacted with deionized water washed Dowex 50 pyridinium ion form resin (for example, 25-50 mesh) either batchwise or by use of a column or similar vessel allowing solvent flow through the resin and out the bottom. This step exchanges castanospermine with the pyridinium ion resulting in pyridine release into solution of the pass-through or batch treatment supernatant. If desired, the amount of castanospermine present in the column pass-through or in the batch treatment supernatant can be determined by LC/MS assay to ensure the resin is not overloaded with castanospermine or to ensure that the maximum amount of castanospermine has been loaded onto the resin for efficient processing.

Excess pyridine can be recovered from any suitable resin wash, column pass-through or batchwise treatment supernatant, or other suitable pyridine containing solution by distillation under reduced pressure such as in a rotary evaporator. Pyridine forms a minimum boiling azeotrope with water allowing simple recovery of excess pyridine. Recovered pyridine can be used to convert Dowex 50 $H^+$ resin to the pyridinium form as needed.

Once this resin has been loaded with castanospermine as desired and washed extensively with deionized water so that the wash is clear and colorless there are two potential methods for elution. The first involves elution (either batchwise or via running solvent through a column) using 2M pyridine in deionized water. In large scale purification procedures castanospermine slowly elutes from the resin over 2 to 3 resin bed volumes of solvent (or more if done batchwise) requiring a significant quantity of pyridine and creating a significant volume of pyridine containing fluid for pyridine recovery. Fractions containing castanospermine can be identified and quantitated by LC/MS or by concentrating a portion to dryness using a rotary evaporator to reveal a white or yellowish precipitate in the evaporator flask. A decision can be made on when to stop the elution based on these results. Castanospermine containing fractions are pooled and concentrated to near dryness, for example, using a rotary evaporator and the castanospermine is then crystallized using either absolute or 95% ethanol and placing the mixture at low temperature (for example, in a freezer) to stimulate crystal formation. Sonication of the crystallization vessel, for example with a bath sonicator, can be used to stimulate crystal formation. The resulting crystals can be harvested by filtration, dried, and stored most suitably in the dark in a freezer. Typical purity of the isolated castanospermine at this step is about 95% or greater.

A second method for elution of the Dowex 50 pyridinium ion form column is with 2 N $NH_4OH$. Under this condition the castanospermine elutes rapidly and with a lower volume of elution solvent. If using a column or similar vessel, collection of fractions should be started immediately. Fraction sizes can be set at any volume convenient for the scale of the process being used. Progress of the elution can be monitored by following the heating front from $NH_4OH$ binding to the resin down the column. Once the heating front has come off the column an odor of $NH_4OH$ will be apparent and collection of fractions should be stopped. Additional $NH_4OH$ can be run over the column to wash additional colored contaminants off the column, and discarded. The castanospermine containing fractions can be identified as described above, pooled, reduced in volume to near dryness, crystalized using absolute or 95% ethanol, and harvested and dried as described above. If using a method for reducing the volume of castanospermine containing fractions that involves warming the solution, for example, under reduced pressure in a rotary evaporator, castanospermine remains stable in temperatures of about 80° C. to 90° C. Alternatively, batch elution with 2N $NH_4OH$ can be conducted using a suitable number of batch elution volumes needed to recover the eluting castanospermine. One consequence of batch elution with 2N $NH_4OH$ compared to use of a column is that the purity can be reduced. Column eluted castanospermine should be about 95% pure whereas batch eluted castanospermine might be 90% to 95% pure at this stage.

7) Further Purification of Castanospermine.

Depending on the purity needs for the isolated castanospermine, additional purification efforts may be needed. Two general methods should be tried initially, recrystallization in ethanol or a repeat of the Dowex 50 pyridinium ion form column step. For recrystallization, crude castanospermine enriched crystals are dissolved in a minimum volume of water and 5- to 10 volumes of absolute or 95% ethanol is added, optionally sonicated, and placed at low temperature (for example in a freezer) to stimulate crystal formation. Crystals are harvested and dried as described above.

Use of a second Dowex 50 pyridinium ion form step is best conducted using a separation column or similar device allowing flow through of solvent through the resin. A separate batch of Dowex 50 pyridinium ion form resin than used in the first such step should be used. This batch of resin can be repeatedly used for this purpose after regeneration as described elsewhere. Crude castanospermine crystals are dissolved in deionized water and loaded onto the column. The capacity of the resin will dictate the maximum amount that can be treated at one time. This can be determined as described above. The column is loaded and washed extensively with deionized water until the effluent is colorless. It is then eluted as before with 2N $NH_4OH$. Castanospermine containing fractions are determined, pooled, concentrated, and the castanospermine crystallized and harvested as described above. Such re-purified castanospermine should be mostly white or very lightly yellow colored and in ≥95% purity at this stage. If castanospermine was eluted using 2M pyridine in the first Dowex 50 pyridinium ion form resin purification step and processed again on a second Dowex 50 pyridinium ion form resin step using elution with 2N $NH_4OH$, white crystals should be obtained that are ≥98% pure castanospermine. After crystallization, harvesting, and drying of the crystals they should be stored in the dark and preferably in a freezer.

8) Regeneration of Dowex 50 Resin Used in Castanospermine Purification.

Dowex 50 resin is used in several purification steps and it can be regenerated time and again for repeated use. If purity of the final product trends down it might be because of the presence and buildup of adsorbed impurities on the resin after repeated use which could justify discarding that resin and starting afresh.

The first step in regeneration of eluted resin is to wash it extensively with water to remove all prior elution solvent and any colored materials present. The resin is then treated with either 2N HCl or 2M H2SO4 in deionized water until the pH of the effluent or batch treatment solution becomes strongly acidic. This is then followed by an additional extensive deionized water wash until the pH rises to about pH5 or higher indicating all free acid has been washed away. For resin intended for the first purification step, this resin is now ready to be used.

To convert resin to the pyridinium ion form, the recycled Dowex 50 H⁺ form resin just prepared is treated with 2N pyridine (the exact concentration is not critical and either fresh or recycled pyridine or some of both can be used). The resin is treated with pyridine until a pyridine odor can be detected in the column effluent or batch treatment supernatant depending on the method used. Then, the resin is washed extensively with deionized water until little or no pyridine odor is detected. It is then ready for use in the appropriate purification steps.

9) LC/MS Assay for Castanospermine.

Typical conditions for LC/MS analysis of castanospermine are as follows.

Sample: a solution of Castanospermine (MW: 189.2) in $H_2O$

MS: Agilent 6410 triple quadrupole mass spectrometer/ AP ESI scan mode, or similar HPLC: Agilent HP1200 with Thermo betasil phenyl column, or similar, under isocratic condition with mobile phase solvent of 0.1% formic acid in 5% Acetonitrile and 95% H2O, column temp: 50 C, flow rate: 0.25 mL/min, 5 uL injection.

FIG. 1: chromatogram

Figure 2:
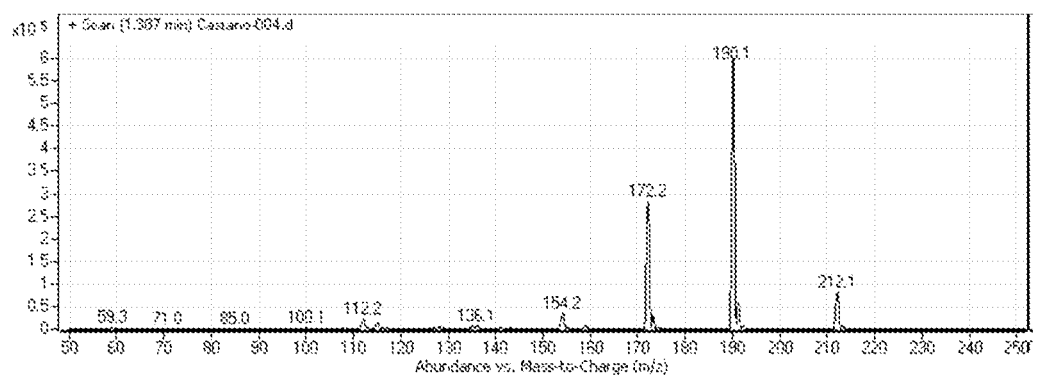
FIG. 2: shows mass spectra (MH+: 190.1, MH–H2O+: 172.2, MH–2H2O+: 154.2, MH–3H2O+: 136.1, M+Na+: 212.1) produced under typical conditions (see Example). The quantity of castanospermine can be assessed based upon the size of MH+ ion at 190.1 AMU in comparison with dilutions and a standard curve.

FIG. 2: mass spectrum (MH+: 190.1, MH−H2O+: 172.2, MH−2H2O+: 154.2, MH−3H2O+: 136.1, M+Na+: 212.1)

Purity of castanospermine can be assessed based upon the chromatogram, and quantity can be assessed based upon the size of the MH+ ion at 190.1 AMU in comparison with dilutions and a standard curve.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for preparing castanospermine, comprising:

(a) separating a liquid fraction comprising castanospermine from castanospermine-containing solid plant material, wherein the castanospermine-containing solid plant material is any castanospermine-containing part or parts of *Castanospermum australe, Alexa* spp., or a combination thereof;

(b) purifying the castanospermine in the liquid fraction from (a) by: (i) mixing the liquid fraction with an ion exchange medium (e.g., ion exchange resin or ion exchange polymer) under conditions that allow castanospermine in the liquid fraction to be bound to the resin, or (ii) column chromatography using a chromatography medium;

(c) eluting the castanospermine from the ion exchange medium of (b)(i) or chromatography medium of (b)(ii) to produce an eluate; and (d) purifying the castanospermine in the eluate of (c) by mixing the eluate with an ion exchange medium (e.g., ion exchange resin or ion exchange polymer) under conditions that allow castanospermine in the eluate to be bound to the ion exchange medium, and eluting the castanospermine.

2. The method of claim 1, wherein the castanospermine-containing plant material comprises castanospermine-containing plant seed material, and wherein the castanospermine-containing plant seed material is prepared for said separating by grinding seeds lacking seed cases, producing ground particles of a size no larger than about 2 millimeters in diameter, and preferably homogenized.

3. The method of claim 1, wherein the castanospermine-containing solid plant material is any castanospermine-containing part or parts of *Castanospermum australe, Alexa* spp., or a combination thereof.

4. The method of claim 1, wherein the castanospermine-containing solid plant material comprises or consists of solid *Castanospermum australe* seed material.

5. The method of claim 4, wherein *C. australe* seed material is prepared by grinding *C. australe* seeds lacking seed cases, producing ground particles of a size no larger than about 2 millimeters in diameter.

6. The method of claim 1, wherein said separating of step (a) includes an ethanol extraction; or wherein said separating of step (a) includes a heat treatment comprising heating the castanospermine-containing solid plant material sufficiently to denature starch within the plant material, allowing the heat-treated plant material to cool, grinding and/or cutting the cooled plant material, and carrying out water extraction on the plant material to obtain the liquid fraction comprising castanospermine.

7. The method of claim 1, wherein said separating of step (a) comprises: (i) allowing the solid material to settle out and placing most of the liquid (first recovered fraction) into a container followed by filtration or centrifugation of the remaining material to remove the rest of the liquid fraction (second recovered fraction) and combining the second recovered fraction with the first recovered fraction; or (ii) directly separating the liquid fraction from the solid material using a continuous process such as centrifugation or filtration.

8. The method of claim 1, wherein the separating of step (a) is repeated one or more times, pooling the obtained liquid fractions from each separation.

9. The method of claim 1, wherein the ion exchange medium of step (b) is an acidic cation exchange medium.

10. The method of claim 1, wherein the ion exchange medium of step (b) comprises ion exchange beads.

11. The method of claim 1, further comprising sampling the mixture after mixing for a duration of time in (b)(i), and measuring the amount of castanospermine remaining in the liquid phase.

12. The method of claim 1, further comprising assaying the amount of castanospermine in the eluted fractions in said eluting step (c) and pooling those fractions with desired high amounts of castanospermine present in order to minimize the amount of impurities carried to the next step.

13. The method of claim 1, wherein said purifying step of (d) is carried out batch-wise, or over a column or other vessel.

14. The method of claim 1, wherein the ion exchange medium of said purifying step of (d) comprises a pyridinium ion form resin, wherein castanospermine is exchanged with the pyridinium ion, resulting in castanospermine bound to the resin and pyridine released into solution.

15. The method of claim 1, wherein castanospermine is eluted in said purifying step (d) using an elution solvent comprising: pyridine in deionized water, or ammonium hydroxide ($NH_4OH$).

16. The method of claim 1, wherein the purity of castanospermine after said purifying step of (d) is at least about 95% if the castanospermine is eluted by a column or other vessel, or about 90% to about 95% if the castanospermine is eluted batch-wise.

17. The method of claim 1, comprising further purifying eluate of step (d).

18. The method of claim 17, wherein said further purifying comprises: (i) repeating the purifying step of (d) on the eluate, or (ii) recrystallizing the castanospermine enriched crystals in the eluate of step (d) with a solvent, such as ethanol, optionally sonicating, placing the solution at reduced temperature to stimulate crystal formation, for harvesting and drying.

19. The method of claim 1, further comprising regenerating the ion exchange medium of step (d).

20. The method of claim 1, further comprising measuring the amount of castanospermine in the product of one or more of steps (a), (b), (c), or (d).

\* \* \* \* \*